United States Patent

Brunken

[11] Patent Number: 5,549,594
[45] Date of Patent: Aug. 27, 1996

[54] SEALING CAP FOR GUIDE TUBES OR REDUCING SLEEVES FOR THE INTRODUCTION OF SURGICAL INSTRUMENTS

[75] Inventor: Dieter Brunken, Hüttblek, Germany

[73] Assignee: Ethicon, Inc., Somerville, N.J.

[21] Appl. No.: 907,002

[22] Filed: Jul. 1, 1992

[30] Foreign Application Priority Data

Jul. 3, 1991 [DE] Germany .......................... 41 21 829.9

[51] Int. Cl.$^6$ .......................................................... A61B 19/00
[52] U.S. Cl. .......................................................... 606/1
[58] Field of Search .................................. 606/1; 604/23, 604/26, 27, 30, 164, 264, 321; 220/260, 269, 306, 356, 771; 215/272, 295, 100 A

[56] References Cited

U.S. PATENT DOCUMENTS

| | | | |
|---|---|---|---|
| 3,151,758 | 10/1964 | Marler | 215/272 |
| 4,084,606 | 4/1978 | Mittleman | 604/30 |
| 4,112,932 | 9/1978 | Chiulli | 604/264 |
| 4,149,535 | 4/1979 | Volder | 604/164 |
| 4,177,814 | 12/1979 | Knepshield et al. | 604/26 |
| 4,653,477 | 3/1987 | Akui et al. | 128/4 |
| 4,723,550 | 2/1988 | Bales et al. | |
| 4,726,374 | 2/1988 | Bales et al. | |
| 4,729,488 | 3/1988 | Bullock | 220/270 |
| 4,809,679 | 3/1989 | Shimonaka et al. | |
| 5,104,379 | 4/1992 | Nakamura et al. | |
| 5,104,383 | 4/1992 | Schichman | |
| 5,104,389 | 4/1992 | Deem et al. | 604/264 |
| 5,114,407 | 5/1992 | Burbank | 604/164 |
| 5,167,644 | 12/1992 | Fischell et al. | 604/264 |

FOREIGN PATENT DOCUMENTS

| | | |
|---|---|---|
| 113520A2 | 7/1984 | European Pat. Off. . |
| 3532560 | 3/1986 | Germany . |

OTHER PUBLICATIONS

Design Application Ser. No. 618,325 Nov. 26, 1990 Reducer For Safety Trocar.

Primary Examiner—Gary Jackson
Assistant Examiner—Glenn Dawson

[57] ABSTRACT

The invention relates to a sealing cap for guide tubes or reducing sleeves for inserting surgical instruments containing an all-round skirt extending down from the end wall of the sealing cap. The internal diameter corresponds to the external diameter of the tubular headpiece of the guide tube or reducing sleeve or is somewhat smaller. Below the end wall is provided a circular groove for receiving an all-round circular flange on the headpiece of the guide tube or reducing sleeve. In the center of the end wall is provided a circular insertion opening for the surgical instrument to be inserted in the guide tube or reducing sleeve. The sealing cap is made from a flexible, natural or synthetic rubber-like material, characterized in that on the lower edge of the skirt is shaped a gripping tongue whose outer boundary edges pass tangentially from two virtually diametrically facing areas of the skirt and pass into one another in a rounded portion on the outer gripping tongue end. On the gripping tongue top and/or bottom an arcuate bead is shaped in the rounded region of the outer gripping tongue end. The circular groove provided below the end wall is spaced from the underside of the end wall.

8 Claims, 1 Drawing Sheet

SEALING CAP FOR GUIDE TUBES OR REDUCING SLEEVES FOR THE INTRODUCTION OF SURGICAL INSTRUMENTS

RELATED APPLICATION

This application claims priority from German Application Serial No. P 41 21 829.9, filed Jul. 3, 1991.

1. Field of the Invention

This invention relates, in general, to laparoscopic surgical devices. More particularly, the invention relates to sealing caps and guide tubes used to allow passage of surgical instruments (such as staplers, graspers and ligating devices) into guide tubes (such as surgical trocars), while maintaining the insufflation used to create pneumoperitoneum within the abdominal cavity during laparoscopic surgery.

2. Background of the Invention

In modern laparoscopic surgery, after inflating the abdominal cavity by passing an inert gas through the cannula of a trocar, the necessary surgical instruments are introduced through this cannula or guide tube for performing minimally invasive surgery. Surgery is controlled by means of an endoscope also introduced into the abdominal cavity and manipulated for carrying out the respective operation, while observing surgery radiologically. Such laparoscopic operations are, e.g., carried out in the gall bladder, stomach and intestinal tract, in gynecological laparoscopy or pelviscopy, for loosening adhesions, or in tubectomies.

The guide tubes hitherto used for this purpose are made from a readily sterilizable, high-quality disposable plastic material or from chrome-nickel-steel alloys, and have at their upper end a plastic sealing plug with a bore contained therein for the for the introduction of the corresponding surgical instrument.

In place of the guide tubes, it is also possible to use reducing sleeves, which have uniform external dimensions and whose internal dimensions are variable to adapt to the surgical instruments to be introduced. By a corresponding sealing cap with a central insertion opening, it is possible to insert surgical instruments with different internal diameters without inert gas pressure loss.

The known plastic sealing plugs for the aforementioned guide tubes or the proposed sealing or packing caps for the reducing sleeves suffer from the disadvantage that they can only be fitted or removed with respect to the headpiece of the surgical trocar with a certain effort, because they are sealingly applied or snapped on in a slightly expanded state. This difficult manipulatability of the sealing caps is made more difficult when using surgical instruments. This further difficulty arises because the surgeons and the operating theatre staff are forced to work with rubber gloves. The problem is only further exacerbated if tissue fluid is present on the gloves, so that handling can be problematical when snapping on or removing the sealing caps.

SUMMARY OF THE INVENTION

An object of the invention is to propose sealing caps useful for laparoscopic surgery, which can be more easily gripped and which also are preferably more easily engaged on or disengaged from the all-round circular flange of the headpiece of a surgical trocar a groove passing around the inside of the sealing cap.

According to the invention this problem is solved by a sealing cap which contains a gripping tongue containing an arcuate bead. This tongue and bead combination affords the user easy positioning placement and removal of the sealing cap on the end of a guide tube (or cannula) of a surgical trocar.

DESCRIPTION OF THE DRAWINGS

The sealing cap according to the invention is described in greater detail hereinafter relative to the drawings, wherein.

DETAILED DESCRIPTION OF THE INVENTION

Figure 1:
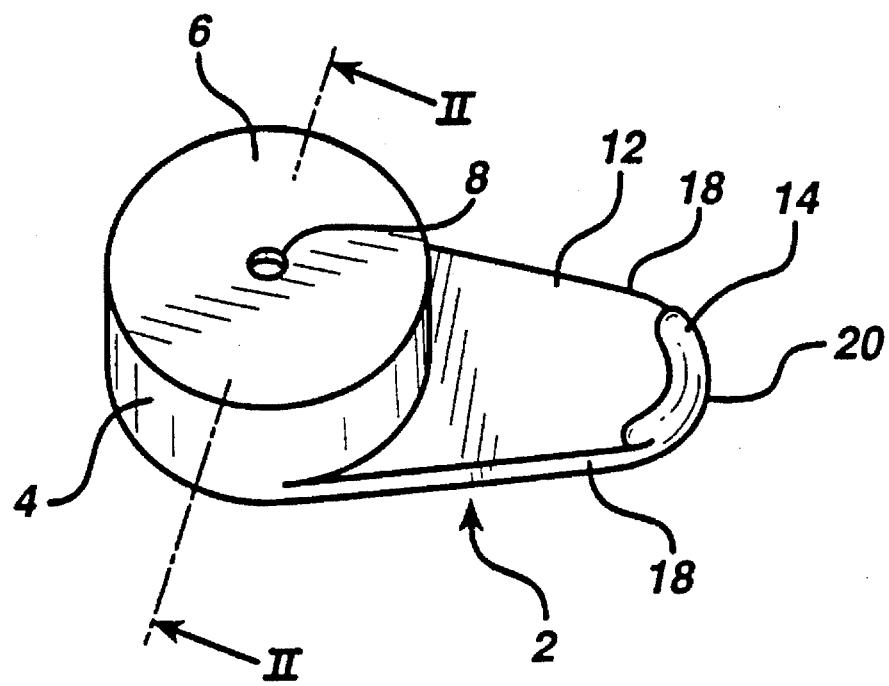
FIG. 1 is a perspective view of the sealing cap of this invention.
Figure 2:
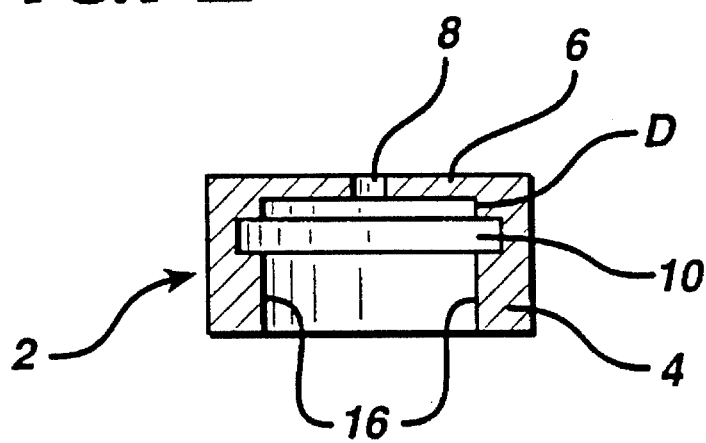
FIG. 2 is a longitudinal section of the sealing cap shown in FIG. 1 taken along line II—II of FIG. 1.

The sealing cap 2 shown in the drawings comprises a tubular lip or skirt 4 with a shaped end wall or top 6, in which there is generally in the center a circular insertion opening 8 for the surgical instrument. The external diameter of the skirt 4 is e.g., 20 mm, while the internal diameter in the present embodiment is approximately 13.8 mm. Accompanied by slight expansion of the skirt 4, such a cap 2 can be applied to the circular headpiece of a guide tube or cannula or a reducing sleeve, useful with such a cannula having an external diameter of approximately 14 mm. The end wall 6 at the top of cap 2 is made thinner than the skirt 4, in order to improve the guidance of the surgical instrument. For instance, in the present case top 6 has a wall thickness of 0.8 mm, while the skirt 4 has a wall thickness of 6.2 mm.

In the upper area of the skirt 4 is provided an all-round groove 10, which permits the snapping engagement of the cap 2 on a circular flange contained on the tubular cannula guide tube, or reducing sleeve (none of which are shown). In the present embodiment, the internal diameter of the circular groove 10 is approximately 16 mm, and, with respect to the inner face 16 of the skirt, has a depth of approximately 2.2 mm.

In a particularly preferred embodiment the circular groove 10 is at a distance D from the underside of the end wall 6, which at least corresponds to the thickness of the latter. This spacing D of 1 mm or more permits an easier fitting or removal by elastic deformation of the skirt 4, also in the upper region. If no such spacing is provided, that is if the groove 10 is located immediately below the lower face of the end wall 6, it is less easy to remove or to lever out from the circular flange of the cannula under elastic deformation the upper skirt part.

In the lower region of the skirt 4 is shaped a gripping tongue 12, whose two outer boundary edges 18 pass approximately tangentially from two virtually diametrically facing areas of the skirt 4 and pass at rounded portion 20 into one another on the outer end of the gripping tongue 12. In the extreme case, the boundary edges 18 can pass from two diametrically facing areas of the skirt 4, but then strictly speaking would be parallel to one another; in that case from the tangential edges 18 there is then a gentle bevel into the rounded portion 20 on the outer gripping tongue end. However, it is sufficient if the boundary edges 18 of the gripping tongue 12 are attached roughly below the cross-section line II—II and run tangentially in such a way that they are at an angle of approximately 15° to 20° to the cross-section line II—II over a length of approximately 1 to 2 cm and then pass into the rounded, outer gripping tongue end portion 20. The gripping tongue length measured from the skirt 4 is preferably 1 to 2 cm or more.

In the outer, rounded portion 20 of the gripping tongue 12 an arcuate bead 14 is shaped onto its top and permits a reliable grasping of the gripping tongue 12. This bead can also be shaped onto the underside and optionally additionally thereon.

Due to the fact that the boundary edges 18 of the gripping tongue 12 engage roughly in the vicinity of the cross-section line II—II of the cap 2, in the case of expanding and raising of the skirt 4, the sealing cap 2 drawn down roughly over half the circumference of the all-round circular flange of the headpiece. The resilient elasticity in the upper region of the skirt 4 is improved in that the circular groove 10 is located at a distance from the underside of the end wall 6 of the cap 2.

The sealing cap 2 can be made from any elastic, flexible natural or synthetic rubber-like material, preference being given to silicone rubber, particularly one having a Shore hardness of 50 to 70.

I claim:

1. Sealing cap for surgical guide tubes or reducing sleeves for inserting surgical instruments comprising: an end wall and an all-around circumferential skirt extending down from said end wall of the sealing cap; and in which below the end wall is provided a circular groove contained within said skirt circumference; and that in the center of the end wall is provided a circular insertion opening having a diameter and capable of accommodating a surgical instrument having substantially the same diameter as said opening diameter to be inserted in the guide tube or reducing sleeve; the sealing cap being made from a flexible material; and characterized in that on the lower edge of the skirt is shaped a gripping tongue, having an end; said tongue containing outer boundary edges which pass tangentially from two virtually diametrically facing positions on said skirt and pass into one another in a founded portion on the end; and on the gripping tongue an arcuate bead is placed in the rounded region of said end.

2. Sealing cap according to claim 1 characterized in that the length of the gripping tongue measured in the radial direction is approximately 1 to 2 cm.

3. Sealing cap according to claim 1 characterized in that the circular groove located below the end wall of the sealing cap is at a distance from the underside of the end wall corresponding to at least the thickness of said end wall.

4. Sealing cap according to claim 1 characterized in that it is made from a silicone rubber with a Shore hardness of 50 to 70.

5. Sealing cap for surgical guide tubes or reducing sleeves for inserting surgical instruments comprising: an end wall having an underside; an all-around circumferential skirt extending from said end wall; a circular groove contained within said skirt circumference and shaped so that it is capable of receiving a flange contained on a guide tube or reducing sleeve, said groove separated from said underside of said end wall by a space therebetween, said space defined by said underside of said end wall and said groove; and an insert opening contained in said end wall, said insert opening capable of receiving therethrough, a shaft of a surgical instrument.

6. The cap of claim 5 wherein said insert opening has a diameter and is capable of receiving therethrough, a shaft of a surgical instrument having an outer diameter substantially the same as the diameter of said opening.

7. The cap of claim 5 wherein said skirt has attached to it a gripping tongue.

8. The cap of claim 7 wherein said tongue has an end portion with a bead placed on said end portion.

* * * * *